US00PP22274P2

(12) United States Plant Patent
Miyazaki

(10) Patent No.: US PP22,274 P2
(45) Date of Patent: Nov. 22, 2011

(54) ***SENECIO* PLANT NAMED 'SUNSENEVIO'**

(50) Latin Name: ***Senecio cruentus*×*Senecio heritierii***
Varietal Denomination: Sunsenevio

(75) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/799,846

(22) Filed: May 4, 2010

(51) Int. Cl.
*A01H 5/00* (2006.01)

(52) U.S. Cl. ..... Plt./480

(58) Field of Classification Search ..... Plt./480
See application file for complete search history.

*Primary Examiner* — Susan McCormick Ewoldt
(74) *Attorney, Agent, or Firm* — C. A. Whealy

(57) ABSTRACT

A new and distinct cultivar of *Senecio* plant named 'Sunsenevio', characterized by its upright and mounded plant habit; freely branching growth habit; freely flowering habit; and large daisy-type inflorescences with purple violet-colored ray florets and darker violet-colored disc florets.

1 Drawing Sheet

Botanical designation: *Senecio cruentus*×*Senecio heritierii.*

Cultivar denomination: 'SUNSENEVIO'.

BACKGROUND OF THE INVENTION

The present invention relates to a new and distinct cultivar of *Senecio* plant, botanically known as *Senecio cruentus*× *Senecio heritierii*, and hereinafter referred to by the name 'Sunsenevio'.

The new *Senecio* plant is a naturally-occurring whole plant mutation of a proprietary selection of *Senecio cruentus*× *Senecio heritierii* identified as code number 6S16-B 326, not patented. The new *Senecio* plant was discovered and selected by the Inventor as a single flowering plant in a controlled greenhouse environment in Higashiomi, Shiga, Japan in February, 2006.

Asexual reproduction of the new *Senecio* plant by terminal cuttings in a controlled greenhouse environment in Higashiomi, Shiga, Japan since March, 2006, has shown that the unique features of this new *Senecio* plant are stable and reproduced true to type in successive generations.

SUMMARY OF THE INVENTION

Plants of the new *Senecio* have not been observed under all possible environmental conditions. The phenotype may vary somewhat with variations in environment such as temperature and light intensity, without, however, any variance in genotype.

The following traits have been repeatedly observed and are determined to be the unique characteristics of 'Sunsenevio'. These characteristics in combination distinguish 'Sunsenevio' as a new and distinct cultivar of *Senecio* plant:

1. Upright and mounded plant habit.
2. Freely branching growth habit.
3. Freely flowering habit.
4. Large daisy-type inflorescences with purple violet-colored ray florets and darker violet-colored disc florets.

Plants of the new *Senecio* differ from plants of the parent selection in the following characteristics:

1. Leaves of plants of the new *Senecio* are lighter green in color than leaves of plants of the parent selection.
2. Plants of the new *Senecio* and the parent selection differ in ray floret color as plants of the parent selection have blue-colored ray florets.

Plants of the new *Senecio* can be compared to plants of *Senecio cruentus*×*Senecio heritieri* 'Sunsenebu', disclosed in U.S. Plant Pat. No. 12,104. In side-by-side comparisons conducted in Higashiomi, Shiga, Japan, plants of the new *Senecio* differed from plants of 'Sunsenebu' in the following characteristics:

1. Plants of the new *Senecio* and 'Sunsenebu' differed in leaf and leaf petiole color.
2. Plants of the new *Senecio* and 'Sunsenebu' differed in ray and disc floret colors as plants of 'Sunsenebu' had violet blue-colored ray and disc florets.

BRIEF DESCRIPTION OF THE PHOTOGRAPHS

The accompanying photographs illustrate the overall appearance of the new *Senecio* plant. These photographs show the colors as true as it is reasonably possible to obtain in colored reproductions of this type. Colors in the photographs may differ slightly from the color values cited in the detailed botanical description which accurately describe the colors of the new *Senecio* plant.

The photograph at the top of the sheet comprises a side perspective view of a typical flowering plant of 'Sunsenevio' grown in a container.

The photograph at the bottom of the sheet is a close-up view of typical inflorescences and inflorescence buds of 'Sunsenevio'.

DETAILED BOTANICAL DESCRIPTION

The aforementioned photographs, following observations and measurements describe plants grown in 15-cm containers during the winter in a polyethylene-covered greenhouse in Higashiomi, Shiga, Japan and under conditions and practices which approximate those generally used in commercial *Senecio* production. During the production of the plants, day temperatures averaged 10° C. and night temperatures averaged 5°

C. Measurements and numerical values represent averages for typical flowering plants. Plants were six months old when the photographs and description were taken. In the following description, color references are made to The Royal Horticultural Society Colour Chart, Fourth Edition, 2001, except where general terms of ordinary dictionary significance are used.

Botanical classification: *Senecio cruentus*×*Senecio heritierii* 'Sunsenevio'.

Parentage: Naturally-occurring whole plant mutation of a proprietary selection of *Senecio cruentus*×*Senecio heritierii* identified as code number 6S16-B 326, not patented.

Propagation:

*Type.*—Terminal vegetative cuttings.

*Time to initiate roots.*—About one week at 20° C.

*Time to produce a rooted young plant.*—About four weeks at 20° C.

*Root description.*—Fine, fibrous; white in color.

*Rooting habit.*—Freely branching.

Plant description:

*Plant form/growth habit.*—Upright and mounded plant habit; daisy-type inflorescences positioned above the foliar plane; freely branching habit; vigorous growth habit.

*Plant height.*—About 46.3 cm.

*Plant diameter.*—About 44.5 cm.

*Lateral branches.*—Length: About 31.6 cm. Diameter: About 3.5 mm. Internode length: About 1.7 cm. Strength: Strong. Texture: Pubescent. Color: Close to 144B tinted with close to 187A.

*Foliage description.*—Arrangement: Alternate, simple. Length: About 6.2 cm. Width: About 7.7 cm. Shape: Cordate. Apex: Acute. Base: Cordate. Margin: Palmately lobed; crenate; slightly undulate. Texture, upper surface: Sparsely pubescent. Texture, lower surface: Densely pubescent. Venation pattern: Pinnate; reticulate. Color: Developing leaves, upper surface: Close to 146B. Developing leaves, lower surface: Close to 148B. Fully expanded leaves, upper surface: Close to 146A; venation, close to 144C. Fully expanded leaves, lower surface: Close to 147B; venation, close to 144C. Petioles: Length: About 6.5 cm. Diameter: About 2.4 mm. Texture, upper and lower surfaces: Sparsely pubescent. Color, upper and lower surfaces: Close to 144C.

Inflorescence description:

*Appearance.*—Large daisy-type inflorescences with narrowly elliptic-shaped ray florets; inflorescences arising from upper leaf axils and positioned above the foliar plane; disc and ray florets developing acropetally on a capitulum; inflorescences face upright and outwardly; freely flowering habit with about 60 inflorescences developing per plant.

*Fragrance.*—Faintly fragrant.

*Natural flowering season.*—In Japan, plants of the new *Senecio* flower continuously from winter to late spring.

*Inflorescence longevity.*—Inflorescences last about two weeks on the plant; inflorescences persistent.

*Inflorescence bud.*—Height: About 8.7 mm. Diameter: About 6.7 mm. Shape: Globose. Color: Close to 191A tinted with close to N186C.

*Inflorescence size.*—Diameter: About 5.8 cm. Depth (height): About 1.1 cm. Disc diameter: About 1.4 cm.

*Ray florets.*—Shape: Narrowly elliptic. Length: About 2.4 cm. Width: About 7 mm. Apex: Obtuse to rounded, slightly praemorse. Base: Obtuse. Margin: Entire. Texture, upper and lower surfaces: Smooth, glabrous; satiny. Number of ray florets per inflorescence: About 13 in a single whorl. Color: When opening, upper surface: More red than N81A. When opening, lower surface: Close to N82C and N80A. Fully opened, upper surface: Lighter than N81A, color becoming closer to lighter than N81B with development. Fully opened, lower surface: Close to N82C and N80A.

*Disc florets.*—Shape: Tubular; apex dentate, five-pointed. Length: About 1 cm. Diameter: About 2.2 mm. Number of disc floret per inflorescence: About 110. Color, immature and mature: Close to 83A.

*Phyllaries.*—Quantity per inflorescence: About 14 in a single whorl. Length: About 7.5 mm Width: About 1.6 mm. Shape: Lanceolate. Apex: Acute. Base: Fused. Margin: Entire. Texture, upper and lower surfaces: Smooth, glabrous. Color, upper and lower surfaces: Close to 137B.

*Peduncles.*—Length: About 3 cm to 5 cm. Diameter: About 1.3 mm. Strength: Strong. Aspect: Mostly upright. Texture: Smooth, glabrous. Color: Close to 144A.

*Reproductive organs.*—Androecium: Present on disc florets only. Anther shape: Ellipsoidal. Anther color: Close to N79A. Pollen amount: Scarce. Pollen color: Close to 9A. Gynoecium: Present on both ray and disc florets. Stigma shape: Bi-parted. Stigma color: Close to N79A.

*Seeds/fruits.*—Seed and fruit development have not been observed on plants of the new *Senecio*.

Disease/pest resistance: Plants of the new *Senecio* have not been observed to be resistant to pathogens and pests common to *Senecio*.

Temperature tolerance: Plants of the new *Senecio* have been observed to tolerate temperatures ranging from about 0° C. to about 30° C.

It is claimed:

1. A new and distinct *Senecio* plant named 'Sunsenevio' as illustrated and described.

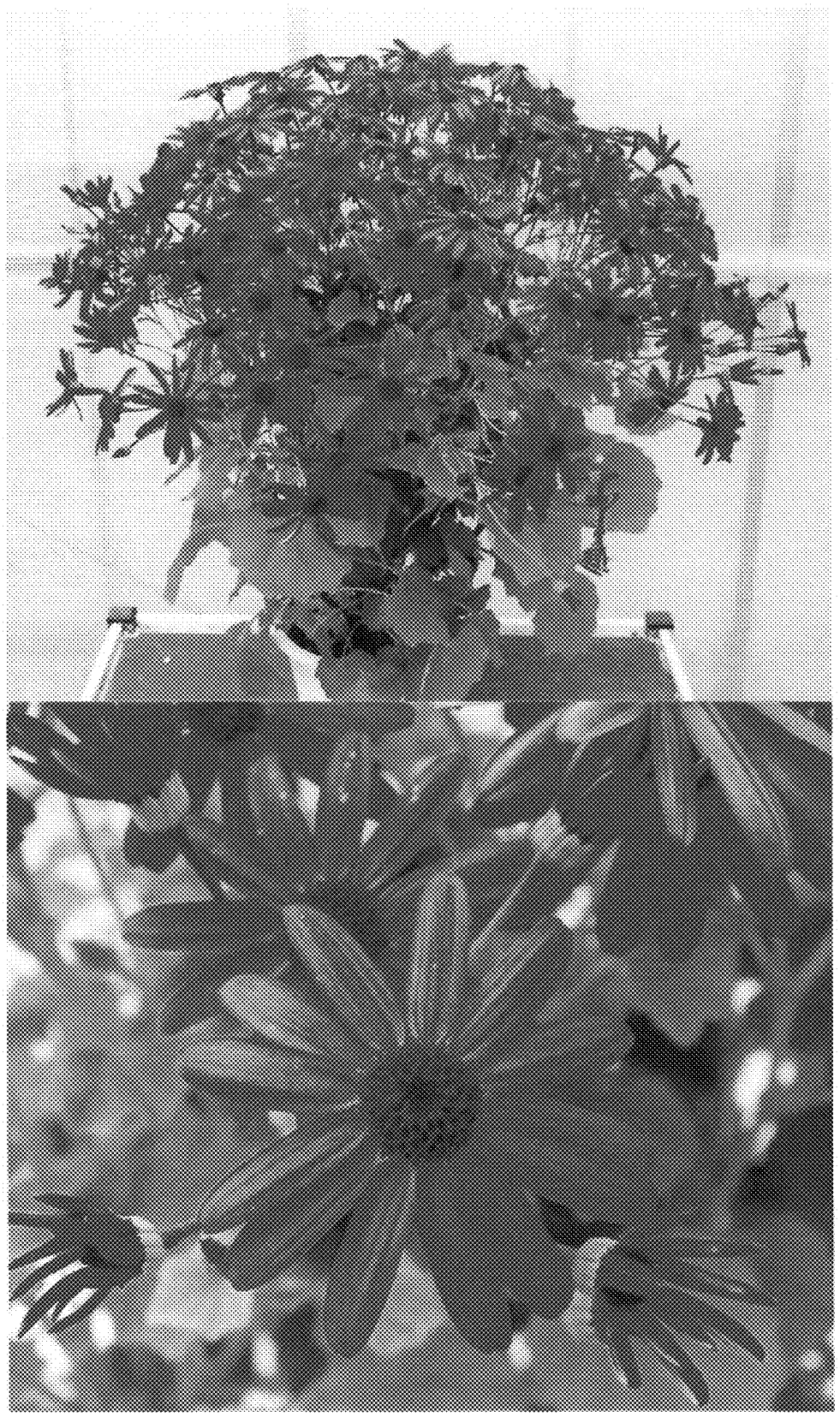

* * * * *